(12) United States Patent
Swain et al.

(10) Patent No.: US 7,196,066 B1
(45) Date of Patent: Mar. 27, 2007

(54) DNA-VACCINES BASED ON CONSTRUCTS DERIVED FROM THE GENOMES OF HUMAN AND ANIMAL PATHOGENS

(75) Inventors: William F. Swain, Madison, WI (US); Lee K. Roberts, Madison, WI (US); Lendon G. Payne, Madison, WI (US); Ralph P. Braun, Madison, WI (US)

(73) Assignee: Powderject Vaccines, Inc., Wilmington, DE (US)

( * ) Notice: Subject to any disclaimer, the term of this patent is extended or adjusted under 35 U.S.C. 154(b) by 0 days.

(21) Appl. No.: 09/705,149

(22) Filed: Nov. 1, 2000

Related U.S. Application Data

(60) Provisional application No. 60/163,297, filed on Nov. 3, 1999.

(51) Int. Cl.
*A61K 31/711* (2006.01)
*C12N 15/86* (2006.01)
*C12N 15/63* (2006.01)
*C07H 21/04* (2006.01)

(52) U.S. Cl. ............... 514/44; 435/320.1; 435/69.1; 435/91.1; 435/91.4; 514/184

(58) Field of Classification Search ............... 424/93.1, 424/93.2, 229.1, 231.1; 435/320.1, 472, 435/476; 514/44, 184
See application file for complete search history.

(56) References Cited

U.S. PATENT DOCUMENTS

| | | | |
|---|---|---|---|
| 4,629,782 A | 12/1986 | Chan et al. | |
| 4,945,050 A | 7/1990 | Sanford et al. | |
| 4,980,286 A | 12/1990 | Morgan et al. | |
| 4,981,782 A | 1/1991 | Judd et al. | |
| 5,036,006 A | 7/1991 | Sanford et al. | |
| 5,091,188 A | 2/1992 | Haynes | |
| 5,100,792 A | 3/1992 | Sanford et al. | |
| 5,120,657 A | 6/1992 | McCabe et al. | |
| 5,149,655 A | 9/1992 | McCabe et al. | |
| 5,171,568 A | 12/1992 | Burke et al. | |
| 5,179,022 A | 1/1993 | Sanford et al. | |
| 5,204,253 A | 4/1993 | Sanford et al. | |
| 5,219,740 A | 6/1993 | Miller et al. | |
| 5,371,015 A | 12/1994 | Sanford et al. | |
| 5,378,814 A | 1/1995 | Houghton et al. | |
| 5,478,744 A | 12/1995 | Sanford et al. | |
| 5,584,807 A | 12/1996 | McCabe | |
| 5,589,466 A | 12/1996 | Felgner et al. | |
| 5,630,796 A | 5/1997 | Bellhouse et al. | |
| 5,658,892 A | 8/1997 | Flotte et al. | |
| 5,738,652 A | 4/1998 | Boyd et al. | |
| 5,851,826 A * | 12/1998 | Fraefel et al. | ............ 435/325 |
| 5,865,796 A | 2/1999 | McCabe | |
| 5,899,880 A | 5/1999 | Bellhouse et al. | |
| 6,004,286 A | 12/1999 | Bellhouse et al. | |
| 6,010,478 A | 1/2000 | Bellhouse et al. | |
| 6,013,050 A | 1/2000 | Bellhouse et al. | |
| 6,168,587 B1 | 1/2001 | Bellhouse et al. | |
| 6,194,389 B1 | 2/2001 | Johnston et al. | |
| 6,573,090 B1 * | 6/2003 | Breakefield et al. | ..... 435/320.1 |
| 6,642,207 B1 * | 11/2003 | Horsburgh et al. | ............ 514/44 |

FOREIGN PATENT DOCUMENTS

| | | |
|---|---|---|
| EP | 0213894 A3 | 3/1987 |
| EP | 0390435 A | 10/1990 |
| WO | WO 89/04669 | 6/1989 |
| WO | WO 89/05349 | 6/1989 |
| WO | WO 90/01949 | 3/1990 |
| WO | WO 90/11089 | 10/1990 |
| WO | WO 90/14436 | 11/1990 |
| WO | WO 91/00359 | 1/1991 |
| WO | WO 91/07487 | 5/1991 |
| WO | WO 93/19183 | 9/1993 |
| WO | WO 94/00575 | 1/1994 |
| WO | WO 94/09819 | 5/1994 |
| WO | WO 94/21797 | 9/1994 |
| WO | WO 94/24263 | 10/1994 |
| WO | WO 95/16779 | 6/1995 |
| WO | WO 95/19799 | 7/1995 |
| WO | WO 95/20660 | 8/1995 |
| WO | WO 96/04947 | 2/1996 |
| WO | WO 96/12513 | 5/1996 |
| WO | WO 96/14855 | 5/1996 |
| WO | WO 96/20022 | 7/1996 |
| WO | WO 96/31613 | 10/1996 |
| WO | WO 97/32987 | 9/1997 |
| WO | WO 97/40163 | 10/1997 |
| WO | WO 97/48485 | 12/1997 |
| WO | WO 98/10750 | 3/1998 |
| WO | WO 98/46263 | 10/1998 |
| WO | WO 99/31262 * | 6/1999 |
| WO | WO 99/43842 | 9/1999 |

OTHER PUBLICATIONS

Braun et al. Virology, 1999, vol. 265, pp. 46-45.*
Tacket et al. Vaccine 1999, vol. 17, pp. 2826-2829.*
Ladmell et al. Vaccine 1998, vol. 16, pp. 115-118.*
Haynes et al. AIDS Research and Human Retroviruses 1994, vol. 10, pp. S43-S45.*
Webster et al. Vaccine 1994, vol. 12, pp. 1495-1498.*
Macklin et al. Journal of Virology 1998, vol. 72, pp. 1491-1496.*

(Continued)

*Primary Examiner*—Bruce R. Campell
*Assistant Examiner*—Bao Qun Li
(74) *Attorney, Agent, or Firm*—Foley & Lardner LLP

(57) ABSTRACT

Methods of eliciting an immune response in a subject by administering one or more large genomic DNA fragments are provided. Also provided are methods of identifying sequences encoding antigenic polypeptides. Also provided are vaccine compositions comprising one or more large genomic DNA fragments.

12 Claims, 3 Drawing Sheets

OTHER PUBLICATIONS

Fynan et al. P.N.A.S. U.S.A. 1993, vol. 90, pp. 11478-11482.*
Barry et al. Vaccine 1997, vol. 15, pp. 788-791.*
Pertmer et al. Vaccine 1995, vol. 15, pp. 1427-1430.*
Boer JG et al. Carcinogenesis. 1992, vol. 13, pp. 15-17.*
Reid et al. Environ Health Perspect. Sep. 1994;102 Suppl 3:57-61.*
Suter et al. Vaccine 1999, vol. 96, No. 22, pp. 12697-13702.*
Hilliard et al. Arch Virol. 1989, vol. 109, No. 1-2, pp. 83-102.*
Samaniego et al. J. Virol. 1998, vol. 72, No. 4, pp. 3307-3320.*
Watnabe et al. Virol. Sep. 20, 2006, No. 1, pp. 1-13.*
Baer et al. (1984) *Nature* 310:207-211.
Davison et al. (1986) *J. Gen. Virol.* 67:1759-1816.
Stanberry et al. (1987) *J. Infect. Dis.* 155:914-920.
McGeoch et al. (1988) *J. Gen. Virol.* 69:1531-1574.
Stanberry et al. (1988) *J. Infect. Dis.* 157:156-163.
Ho et al. (1989) *J. Virol.* 63:2951-2958.
Burke et al. (1991) *Virology* 181:793-797.
Burke et al. (1991) *Rev. Infect. Dis.* 13(Suppl 11):S906-S911.
Houghton et al. (1991) *Hepatology* 14:381-388.
Mertz et al. (1992) *Ann. Intern. Med.* 116:197-202.
Straus et al. (1994) *Lancet* 343:1460-1463.
Johnston et al. (1997) *Vaccine* 15:808-809.
Swain et al. (1997) *Behring Institute* 98:73-78.
Remington's Pharmaceutical Sciences (1980) Mark Publishing Company, Pennsylvania, pp. 1483-1484.
Townsend et al. (1984) Cell 39: pp. 13-25.
Townsend et al. (1985) Prog. Allergy 36: pp. 10-43.
Sanford et al. (1987) Particulate Science and Technology 5: pp. 27-37.
Klein et al. (1987) Nature 327: pp. 70-73.
Tang et al. (1988) J. Virology 62:4745-4751.
Zelenin et al. (1989) FEBS Letters 244: pp. 65-67.
Milich (1989) Advances in immunology 45: pp. 195-282.
S.A. Johnston (1990) "Biolistic transformation: microbes to mice," Nature 346: pp. 776-777.
Poznansky et al. (1991) J. Virology 65: pp. 532-536.
Haynes et al. (1991) Molecular Immunology 28: pp. 231-234.
Rhim et al. (1991) J. Virology 65: pp. 4555-4564.
Rousseaux-Prevost et al. (1991) Molecular Immunology 28: pp. 943-949.
Sedegah et al. (1994) Proc. Natl. Acad. Sci. USA 91: pp. 9866-9870.
Fynan et al. (1995) Int. J. Immunopharmac. 17: pp. 79-83.
Sarphie et al. (1997) J. Controlled Release 47: pp. 61-69.
Suter et al. (1999) Proc. Natl. Acad. Sci. USA 96: pp. 12697-12702.
Rippie, E.G., Ph.D. (1980) Pharmaceutical Sciences, Marck Publishing Company, Pennsylvania, pp. 1535-1552.
Saeki et al., "Herpes Simplex Virus Type 1 DNA Amplified as Bacterial Artificial Chromosome in *Escherichia coli*: Rescue of Replication-Competent Virus Progeny and Packaging of Amplicon Vectors," *Human Gene Therapy* 9:2787-2794 (1998).

* cited by examiner

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:artificial
      construct

<400> SEQUENCE: 1
tccatgacgt tcctgatgct                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:artificial -continued

```
      construct

<400> SEQUENCE: 2
atcgactctc gagcgttctc                                                20

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:artificial
      construct

<400> SEQUENCE: 3
cgcgtctaga aacgttcgcg accacgggtg ac                                  32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:artificial
      construct

<400> SEQUENCE: 4
cgcgtctaga tgatggggtc ccgctaactc gc                                  32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:artificial
      construct

<400> SEQUENCE: 5
cgcgtctaga ccttcatgac cgcgctggtc ct                                  32
```

DNA-VACCINES BASED ON CONSTRUCTS DERIVED FROM THE GENOMES OF HUMAN AND ANIMAL PATHOGENS

CROSS-REFERENCE TO RELATED APPLICATION

This application is related to U.S. provisional application Ser. No. 60/163,297, filed 3 Nov. 1999, from which priority is claimed pursuant to 35 U.S.C. §119(e)(1) and which application is incorporated herein by reference in its entirety.

TECHNICAL FIELD

The present invention relates generally to vaccine compositions and methods of use thereof. More particularly, the invention pertains to eliciting an immune response in a subject by administering one or more large genomic DNA fragments to the subject.

BACKGROUND

Vaccines which induce a cell-mediated immune response are emerging as important strategies in combating parasites, autoimmune disorders, allergic diseases and cancers. Conventional vaccination strategies generally involve administration of either "live" or "dead" vaccines. Ertl et al. (1996) *J. Immunol.* 156:3579–3582. The so-called live vaccines include attenuated microbes and recombinant molecules based on a living vector. The dead vaccines include those based on killed whole pathogens, and subunit vaccines, e.g., soluble pathogen subunits or protein subunits. Live vaccines are generally successful in providing an effective immune response in immunized subjects; however, such vaccines can be dangerous in immunocompromised or pregnant subjects, can revert to pathogenic organisms, or can be contaminated with other pathogens. Hassett et al. (1996) *Trends in Microbiol.* 8:307–312. Dead vaccines avoid the safety problems associated with live vaccines; however such vaccines often fail to provide an appropriate and/or effective immune response in immunized subjects.

More recently, direct injection of plasmid DNA by intramuscular (Wolff et al. (1990) *Science* 247:1465:1468) or intradermal injection with a needle and syringe (Raz et al. (1994) *PNAS USA* 91:9519–9523) has been described. Another approach referred to as ballistic or particle-mediated DNA delivery employs a needless particle delivery device to administer DNA-coated microscopic gold beads directly into the cells of the epidermis. (Yang et al. (1990) *PNAS USA* 87:9568–9572). Thus, a number of delivery techniques can be used to deliver nucleic acids for immunizations, including particle-mediated techniques which deliver nucleic acid-coated microparticles into target tissue (see, e.g., co-owned U.S. Pat. No. 5,865,796, issued Feb. 2, 1999). Particle-mediated nucleic acid immunization techniques have been shown to elicit both humoral and cytotoxic T lymphocyte immune responses following epidermal delivery of nanogram quantities of DNA. Pertmer et al. (1995) *Vaccine* 13:1427–1430. Such particle-mediated delivery techniques have been compared to other types of nucleic acid inoculation, and found markedly superior. Fynan et al. (1995) *Int. J. Immunopharmacology* 17:79–83, Fynan et al. (1993) *Proc. Natl. Acad. Sci. USA* 90:11478–11482, and Raz et al. (1994) *Proc. Natl. Acad. Sci. USA* 91:9519–9523.

A novel transdermal drug delivery system that entails the use of a needleless syringe to deliver solid drug-containing particles in controlled doses into and through intact skin has also been described. In particular, commonly owned U.S. Pat. No. 5,630,796 to Bellhouse et al., describes a particle delivery device (e.g., a needleless syringe) that delivers pharmaceutical particles entrained in a supersonic gas flow. The particle delivery device is used for transdermal delivery of powdered drug compounds and compositions, for delivery of genetic material into living cells (e.g., gene therapy) and for the delivery of biopharmaceuticals to skin, muscle, blood or lymph. The device can also be used in conjunction with surgery to deliver drugs and biologics to organ surfaces, solid tumors and/or to surgical cavities (e.g., tumor beds or cavities after tumor resection). Pharmaceutical agents that can be suitably prepared in a substantially solid, particulate form can be safely and easily delivered using such a device.

One particular particle delivery device generally comprises an elongate tubular nozzle having a rupturable membrane initially closing the passage through the nozzle and arranged substantially adjacent to the upstream end of the nozzle. Particles of a therapeutic agent to be delivered are disposed adjacent to the rupturable membrane and are delivered using an energizing means which applies a gaseous pressure to the upstream side of the membrane sufficient to burst the membrane and produce a supersonic gas flow (containing the pharmaceutical particles) through the nozzle for delivery from the downstream end thereof. The particles can thus be delivered from the needleless syringe at delivery velocities of between Mach 1 and Mach 8 which are readily obtainable upon the bursting of the rupturable membrane.

Another particle delivery device configuration generally includes the same elements as described above, except that instead of having the pharmaceutical particles entrained within a supersonic gas flow, the downstream end of the nozzle is provided with a bistable diaphragm which is moveable between a resting "inverted" position (in which the diaphragm presents a concavity on the downstream face to contain the pharmaceutical particles) and an active "everted" position (in which the diaphragm is outwardly convex on the downstream face as a result of a supersonic shockwave having been applied to the upstream face of the diaphragm). In this manner, the pharmaceutical particles contained within the concavity of the diaphragm are expelled at a high initial velocity from the device for transdermal delivery thereof to a targeted skin or mucosal surface.

Transdermal delivery using the above-described device configurations is generally carried out with particles having an approximate size that generally ranges between 0.1 and 250 μm. Particles larger than about 250 μm can also be delivered from the device, with the upper limitation being the point at which the size of the particles would cause untoward damage to the skin cells. The actual distance which the delivered particles will penetrate depends upon particle size (e.g., the nominal particle diameter assuming a roughly spherical particle geometry), particle density, the initial velocity at which the particle impacts the skin surface, and the density and kinematic viscosity of the skin. Target particle densities for use in needleless particle injection generally range between about 0.1 and 25 g/cm$^3$, and injection velocities generally range between about 150 and 3,000 m/sec.

The level of effective protection achieved with DNA-vaccines is similar to that elicited by traditional protein subunit vaccines and killed or attenuated viral vaccines; but is traditionally less than that observed in convalescent animals following recovery from a natural infection. Manickan et al. (1997) *Critical Review Immunol.* 17:139–154.

Herpes infections are extremely prevalent and are caused by two viruses, herpes simplex virus type 1 (HSV-1) and herpes simplex virus type 2 (HSV-2). HSV-1 is usually acquired in childhood and is the predominant cause of oral infections. HSV-2 infections are usually associated with sexually transmitted genital infections. However, up to 25% of genital herpes is caused by HSV-1. Natural infection appears to impart cross-protection between the two HSV strains, in that, individuals infected with one strain (e.g., HSV-1) have a low incidence of infection with the other strain (i.e., HSV-2) despite exposure. Mertz et al. (1992) *Ann. Intern. Med.* 116:197–202. The reasons for these observations have not been fully elucidated. Although near complete protection against infection with herpes simplex virus (HSV) can be achieved in mice and/or guinea pigs by vaccination with killed or modified virus, the degree of protection in convalescent animals sets the target for improvement of vaccine performance.

HSV is a double-stranded DNA virus having a genome of about 150–160 kbp. HSV-1 and HSV-2 genomes are colinear and share greater than 50% homology over the entire genome. For some genes, the amino acid identity between the two virus types is as much as 80 to 90%. As a result of this similarity, many HSV-specific antibodies are cross-reactive for both virus types.

The viral genome is packaged within an icosahedral nucleocapsid which is enveloped in a membrane. The membrane (or envelope) includes at least 10 virus-encoded glycoproteins, the most abundant of which are gB, gC, gD, and gE. The viral glycoproteins are involved in the processes of virus attachment to cellular receptors and in fusion of the viral and host cell membranes to permit virus entry into the cell. The glycoproteins are located on the surface of the virion. Consequently, they are targets of neutralizing antibody and antibody dependent cell cytotoxicity (ADCC). Within a virus type, there is a limited (1 to 2%) strain-to-strain sequence variability of the glycoprotein genes. The viral genome also encodes over 70 other proteins, including virion proteins, such as VP16 and VP22 which are associated with the virion tegument, located between the capsid and the envelope. In addition, a group of approximately five ICPs are encoded by the virus. (See, e.g., WO/9516779 regarding ICP4-containing vaccines). These early proteins are synthesized early in the viral replication cycle, in contrast to the envelope glycoproteins which are only made late in the life cycle of the virus.

For a review of the molecular structure and organization of HSV, see, for example, Roizman and Sears (1996) "Herpes simplex viruses and their replication" in Fields Virology, 3rd ed., Fields et al. eds., Lippincott-Raven Publishers, Philadelphia, Pa.

One approach to HSV vaccine development has been the use of isolated glycoproteins which have been shown to be both protective and therapeutic. See, e.g., Burke et al., *Virology* (1991) 181:793–797; Burke et al., *Rev. Infect. Dis.* (1991) 13(Suppl 11):S906–S911; Straus et al., *Lancet* (1994) 343:1460–1463; Ho et al., *J. Virol.* (1989) 63:2951–2958; Stanberry et al., *J. Infect. Dis.* (1988) 157:156–163; and Stanberry et al., (1987) *J. Infect. Dis.* 155:914–920; Stanberry, L. R. "Subunit Viral Vaccines: prophylactic and therapeutic use." In: Aurelian L (ed.) *Herpesviruses, the Immune Systems and Aids*. Kluwer, Boston, pp. 309–341. However, clinical trials have failed to demonstrate significant protective immunity in humans vaccinated with a subunit vaccine consisting of the gB and gD glycoproteins.

One method of identifying sequences encoding immunogenic epitopes involves the use of expression libraries, and is known as expression library immunization (ELI). International Publication WO 96/31613 reports that introducing cloned expression libraries from cDNA or fragmented genomic DNA into a subject induces an immune response which can be quantified to select libraries including sequences with immunogenic epitopes. Selected pools are then identified and further characterized. The genomic fragments used are relatively small, between about 10 and 100 base pairs in length. Moreover, in the ELI method, genomic fragments are spliced into a vector having an exogenous (e.g., heterologous) promoter. The genomic clones of ELI remain unidentified sequences and, accordingly, any antigenic sequences must be extensively purified and characterized before a specific vaccine can be developed.

Despite these reports, there remains a need for methods of eliciting an immune response that more closely mimics an animal's natural response to antigens. The present invention provides a solution to this and other problems.

SUMMARY OF THE INVENTION

The present invention provides methods and compositions for eliciting immune responses in a subject. In one aspect, the invention includes a method for eliciting an immune response in a vertebrate subject comprising administering constructs carrying genomic DNA fragments obtained or derived from one or more pathogens. Once the genomic DNA fragments have been administered to the subject, antigen encoded by coding sequences present in the genomic DNA fragments is expressed at an amount sufficient to elicit an immune response. The genomic fragments are preferably greater than 5 kilobases (kb) in size. In certain embodiments, the construct is a plasmid carrying genomic DNA fragments between about 5 kb and 25 kb size. In yet other embodiments the construct is a cosmid carrying genomic DNA fragments between about 25 kb and about 50 kb in size. In certain embodiments, expression of coding sequences (i.e., antigen coding sequences) contained within the genomic DNA fragments is not driven by a heterologous promoter. The pathogens may be, for example, one or more types of bacteria or one or more types of viruses (e.g., a herpes simplex virus or "HSV"). The constructs (e.g., plasmids or cosmids) may be administered, for example, by transdermal administration.

In another aspect, the invention includes a method for eliciting an immune response in a vertebrate subject. The method includes the steps of: (a) providing a core carrier coated with constructs carrying genomic DNA fragments obtained or derived from one or more pathogens, wherein the genomic DNA fragments contain an antigen coding sequence; and (b) administering the coated core carrier to the subject using a particle-mediated transdermal delivery technique, whereby antigen encoded by a coding sequence present in the genomic DNA fragments is expressed in the subject in an amount sufficient to elicit an immune response. The genomic DNA fragments are greater than about 5 kilobases in size. In certain embodiments, the construct is a plasmid and carries genomic DNA fragments ranging from about 5 to about 25 kilobases in size. In other embodiments, the construct is a cosmid and carries genomic DNA fragments from about 25 to about 50 kilobases in size. In certain embodiments, expression of coding sequences contained within the genomic DNA fragments of the construct (e.g., plasmid or cosmid) is not driven by a heterologous promoter. For any of the plasmid or cosmid constructs described herein, the core carrier typically has an average diameter of about 0.5 to about 5 μm and a density sufficient to allow transdermal delivery into the subject. The core carrier can be comprised of a metal, for example, gold. The pathogens can be, for example, one or more types of bacteria, one or more viruses, or can be derived from two or more different pathogens. In other embodiments, the methods involve repeating step (b) to provide a prime and a booster administration.

In another aspect of the invention, a method is provided for identifying a sequence encoding an antigenic polypeptide. The method entails the steps of: (a) administering constructs carrying genomic DNA fragments obtained or derived from one or more pathogens, wherein the genomic DNA fragments contain or are suspected of containing a coding sequence for the antigenic polypeptide and, upon delivery to the subject, the antigenic polypeptide is expressed from the coding sequence in an amount sufficient to elicit an immune response; and (b) identifying the sequence on the construct encoding the antigenic polypeptide. In one embodiment, step (b) comprises administering one or more fragments of the constructs of step (a) and identifying which fragment encodes the antigenic polypeptide. In another embodiment, step (b) comprises sequencing the construct.

In yet another aspect, the invention includes a vaccine composition comprising one or more constructs carrying genomic DNA fragments obtained or derived from one or more pathogens, for example, a vaccine composition comprising one or more constructs (e.g., clone #68) carrying genomic DNA fragments from herpes simplex virus-2 (HSV-2). In certain embodiments, the construct is a plasmid carrying genomic DNA fragments ranging from about 5 kb to 25 kb in size. In yet other embodiments the construct is a cosmid carrying genomic DNA fragments ranging from about 25 kb to about 50 kb in size. In any of the methods or compositions described herein, the genomic fragments can include the immediate early regions (e.g., ICP27, ICP0, ICP4, ICP22, etc.) of a virus such as HSV-2, for example the region spanning from approximately nucleotide 114589 to 134980 of the HSV-2 genome, or an EcoRI fragment that spans nucleotides 110931 to 139697 of the HSV-2 genome. The sequence of the HSV-2 genome is available form published sources, for example the sequence deposited with GenBank under Accession Number NC_001798. In certain embodiments, expression of coding sequences contained within the genomic DNA fragments of the construct (e.g., plasmid or cosmid) is not driven by a heterologous promoter. The vaccine compositions may also comprise one or more adjuvants.

These and other embodiments of the present invention will readily occur to those of ordinary skill in the art in view of the disclosure herein.

MODES FOR CARRYING OUT THE INVENTION

Figure 1:
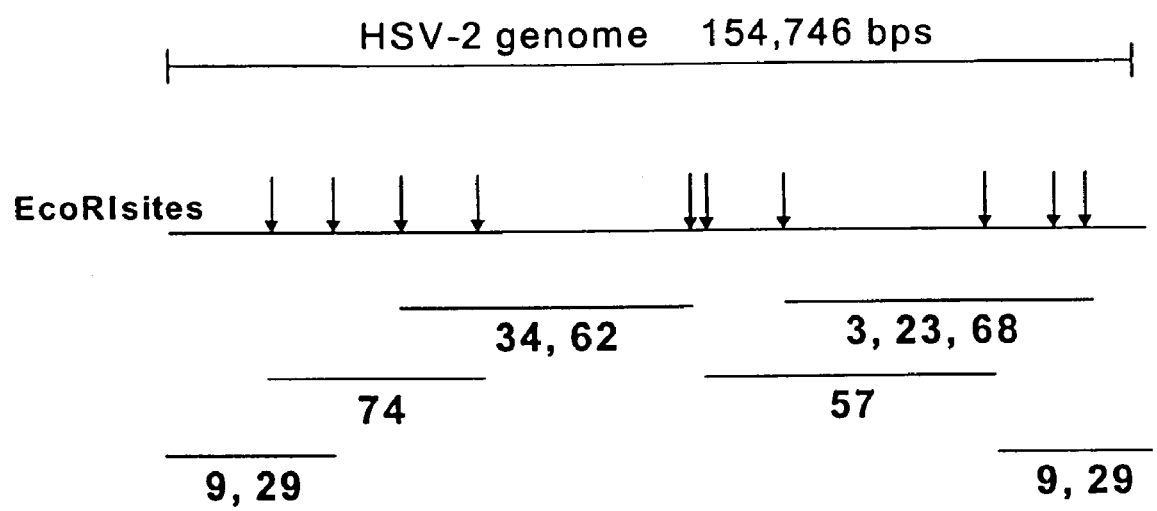
FIG. 1 is a schematic representation of various HSV-2 cosmids used in the present invention. The numbers represent the designations for the cosmid clones that have been used to immunize animals. Each cosmid contains approximately 30,000–40,000 base pairs of DNA from HSV-2.

Before describing the present invention in detail, it is to be understood that this invention is not limited to particular antigens or to antigen-coding nucleotide sequences. It is also to be understood that different applications of the disclosed methods may be tailored to the specific needs in the art. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a", "an", and "the" include plural referents unless the content clearly dictates otherwise. Thus, for example, reference to "an antigen" includes a mixture of two or more such agents, reference to "a particle" includes reference to mixtures of two or more particles, reference to "a recipient cell" includes two or more such cells, and the like.

Definitions

Unless defined otherwise, all technical and scientific terms used herein have the same meaning as commonly understood by one of ordinary skill in the art to which the invention pertains. The following terms are intended to be defined as indicated below.

The term "vaccine composition" intends any pharmaceutical composition containing an antigen (e.g., polynucleotide encoding an antigen), which composition can be used to prevent or treat a disease or condition in a subject. The term thus encompasses both subunit vaccines, i.e., vaccine compositions containing antigens which are separate and discrete from a whole organism with which the antigen is associated in nature, as well as compositions containing whole killed, attenuated or inactivated bacteria, viruses, parasites or other microbes.

The term "transdermal" delivery intends intradermal (e.g., into the dermis or epidermis), transdermal (e.g., "percutaneous") and transmucosal administration, i.e., delivery by passage of an agent into or through skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1–3, Kydonieus and Berner (eds.), CRC Press, (1987). Thus, the term encompasses delivery from a particle delivery device (e.g., needleless syringe) as described in U.S. Pat. No. 5,630,796, as well as particle-mediated delivery as described in U.S. Pat. No. 5,865,796.

By "core carrier" is meant a carrier particle on which a nucleic acid (e.g., DNA) is coated in order to impart a defined particle size as well as a sufficiently high density to achieve the momentum required for cell membrane penetration, such that the DNA can be delivered using particle-mediated delivery techniques, for example those described in U.S. Pat. No. 5,100,792. Core carriers typically include materials such as tungsten, gold, platinum, ferrite, polystyrene and latex. See e.g., *Particle Bombardment Technology for Gene Transfer*, (1994) Yang, N. ed., Oxford University Press, New York, N.Y. pages 10–11.

By "particle delivery device," or "needleless syringe," is meant an instrument which delivers a particulate composition transdermally, without a conventional needle that pierces the skin. Particle delivery devices for use with the present invention are discussed throughout this document.

By "antigen" is meant a molecule which contains one or more epitopes that will stimulate a host's immune system to make a cellular antigen-specific immune response, or a humoral antibody response. Thus, antigens include proteins, polypeptides, antigenic protein fragments, oligosaccharides, polysaccharides, and the like. Furthermore, the antigen can be derived from any known virus, bacterium, parasite, plants, protozoans, or fungus, and can be a whole organism. The term also includes tumor antigens. Similarly, an oligonucleotide or polynucleotide which expresses an antigen, such as in DNA immunization applications, is also included in the definition of antigen. Synthetic antigens are also included, for example, polyepitopes, flanking epitopes, and other recombinant or synthetically derived antigens (Bergmann et al. (1993) Eur. J. Immunol. 23:2777–2781; Bergmann et al. (1996) J. Immunol. 157:3242–3249; Suhrbier, A. (1997) Immunol. and Cell Biol. 75:402–408; Gardner et al. (1998) 12th World AIDS Conference, Geneva, Switzerland, Jun. 28-Jul. 3, 1998).

By "suitable immune response" is meant that the methods of the invention can bring about in an immunized subject an immune response characterized by the production of B and/or T lymphocytes specific for an antigen or antigens.

The term "peptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

The term "pathogen" is used in a broad sense to refer to the source of any molecule that elicits an immune response. Thus, pathogens include, but are not limited to, virulent or attenuated viruses, bacteria, fungi, protozoa, parasites, cancer cells and the like. Typically, the immune response is elicited by one or more peptides produced by these pathogens. As described in detail below, genomic DNA encoding the antigenic peptides from these and other pathogens is used to generate an immune response that mimics the response to natural infection. It will also be apparent in view of the teachings herein, that the methods include the use of genomic DNA obtained from more than one pathogen.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the linear representation of a polynucleotide molecule. This linear representation can be input into databases in a computer having a central processing unit and used for bioinformatics applications such as functional genomics and homology searching.

A "vector" is any moiety capable of transferring gene sequences to target cells (e.g., viral vectors, non-viral vectors, particulate carriers, and liposomes). A "plasmid" vector is an extrachromosomal genetic element which is capable of self-replication in a host cell. A "cosmid" vector is a special type of plasmid vector that uses the cos sequences of bacteriophage lambda (λ). The term "cos ends" or "cos sites" refers to the single stranded 12 base pair complementary extensions of λ DNA. Cosmids can carry large inserts, for example up to around 50 kb in size, while typical plasmids carry fragments under about 10 kb in size. Because of their capacity to carry large fragments, cosmids are useful for the construction of genomic libraries. Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors. A "genomic library" is a collection of recombinant nucleic acid molecules which together represent the entire genome of an organism.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Transcription and translation of coding sequences are typically regulated by "control elements," including, but not limited to, transcription promoters, transcription enhancer elements, Shine and Delagamo sequences, transcription termination signals, polyadenylation sequences (located 3' to the translation stop codon), sequences for optimization of initiation of translation (located 5' to the coding sequence), and translation termination sequences.

A "promoter" is a nucleotide sequence which directs transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith. A sequence is "derived or obtained from" a molecule if it has the same or substantially the same basepair sequence as a region of the source molecule, its cDNA, complements thereof, or if it displays sequence identity as described below.

"Operably linked" refers to an arrangement of elements wherein the components so described are configured so as to perform their usual function. Thus, a given promoter that is operably linked to a coding sequence (e.g., encoding an antigen of interest) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the NIBI internet website.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. For example, stringent hybridization conditions can include 50% formamide, 5× Denhardt's Solution, 5×SSC, 0.1% SDS and 100 µg/ml denatured salmon sperm DNA and the washing conditions can include 2×SSC, 0.1% SDS at 37° C. followed by 1×SSC, 0.1% SDS at 68° C. Defining appropriate hybridization conditions is within the skill of the art. See, e.g., Sambrook et al., supra; *DNA Cloning, supra; Nucleic Acid Hybridization, supra.*

As used herein the term "adjuvant" refers to any material that enhances the action of a drug, antigen, polynucleotide, vector or the like. It is intended, although not always explicitly stated, that molecules having similar biological activity as wild-type or purified peptide adjuvants (e.g., recombinantly produced or muteins thereof) and nucleic acid encoding these molecules are intended to be used within the spirit and scope of the invention.

As used herein, the term "treatment" includes any of following: the prevention of infection or reinfection; the reduction or elimination of symptoms; and the reduction or complete elimination of a pathogen. Treatment may be effected prophylactically (prior to infection) or therapeutically (following infection).

By "vertebrate subject" is meant any member of the subphylum cordata, particularly mammals, including, without limitation, humans and other primates. The term does not denote a particular age. Thus, both adult and newborn individuals are intended to be covered.

General Overview of the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

The present invention provides novel methods of eliciting an immune response in a subject. Briefly, vector libraries carrying large polynucleotide (e.g., DNA) fragments representing the genomes of one or more pathogens (e.g., cells, tissues, viruses, etc.) are generated. The vectors are typically in the form of plasmids or cosmids, depending upon the size of the genomic fragments. The libraries may contain overlapping or non-overlapping inserts. One or more selected clones of the genomic library are then administered to a subject in an amount effective to elicit an immune response. In this way, a large number of antigens (and their corresponding epitopes) can be administered to the subject in a single immunization step. In addition, because the large genomic fragments carried by the constructs (e.g., cosmids or plasmids) include their endogenous expression control elements, further molecular manipulations (for example insertion of heterologous promoter sequences to drive expression from coding sequences present in the genomic fragments) are not required. However, heterologous control may be present in the constructs, for example when the genomic sequences are derived from procaryotes such as bacteria. Further, because the endogenous control elements (e.g., cis and/or trans-acting regulatory elements) drive antigen expression in the host subject and the immunogenic gene-products are thus produced at levels similar to that of a natural infection, the overall immune response elicited by the constructs more closely mimics the response due to natural infection. In contrast, the use of heterologous promoters in previously described expression library immunization would result in non-selective expression of the pathogen's genes.

The invention also includes an efficient method for identifying sequences encoding antigenic fragments. In particular, use of constructs having a known genetic composition allows for a method of identifying sequences that encode antigenic polypeptides. For example, a cosmid or plasmid clone that induces an immune response in a subject is identified. The precise sequence(s) involved in the immune response can then be determined by methods known in the art, for example sequencing of the clone, or by further fragmenting of the cosmid or plasmid insert and testing these smaller fragments for their immunogenicity.

The polynucleotides of the present invention may be introduced into cells in vitro or in vivo, for example by conventional transfection techniques or by coating the polynucleotides onto particles and then administering the coated particles to the cells using particle-mediated transfection. Alternatively, the polynucleotides may be provided in a particulate (e.g., powder) form, discussed more fully below and in the disclosure of International Publication Number WO 98/10750, which is incorporated by reference herein.

Advantages of the present invention include, but are not limited to, (i) expanding the number of antigens used to elicit an immune response; (ii) providing an array of antigens (e.g., epitopes) which more closely mimics that of a natural infection; (iii) achieving co-delivery of the antigens and their associated wild-type regulatory elements into the same cell to achieve coordinated expression of multiple antigens; (iv) eliciting an immune response similar to that elicited by natural infection; (v) eliciting an immune response that is more protective than that elicited by natural infection, e.g., by elimination of an immunodominant antigen or elimination of genes that inhibit immune responses; (vi) identifying the most effective combination of antigens for subsequent production of plasmids for use in eliciting an immune response; and (vii) triggering the antigen processing and presentation pathways that are normally involved in the clearance of intracellular infections.

Antigens

The methods described herein are useful in eliciting an immune response against a wide variety of cells, tissues and human or animal pathogens. These pathogens contain one or more antigens. Non-limiting examples of sources for genomic DNA for cosmid or plasmid libraries include viruses, bacterial cells, fungal cells, and other pathogenic organisms.

Suitable viral antigens include, but are not limited to, those obtained or derived from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV). See, e.g., International Publication Nos. WO 89/04669; WO 90/11089; and WO 90/14436. The HCV genome encodes several viral proteins, including E1 and E2. See, e.g., Houghton et al. (1991) $Hepatology$ 14:381–388. Genomic fragments containing sequences encoding these proteins, as well as antigenic fragments thereof, will find use in the present methods. Similarly, the coding sequence for the δ-antigen from HDV is known (see, e.g., U.S. Pat. No. 5,378,814).

In like manner, a wide variety of proteins from the herpesvirus family can be used as antigens in the present invention, including proteins derived from herpes simplex virus (HSV) types 1 and 2, such as HSV-1 and HSV-2 glycoproteins gB, gD and gH; antigens from varicella zoster virus (VZV), Epstein-Barr virus (EBV) and cytomegalovirus (CMV) including CMV gB and gH; and antigens from other human herpesviruses such as HHV6 and HHV7. (See, e.g. Chee et al. (1990) $Cytomegaloviruses$ (J. K. McDougall, ed., Springer-Verlag, pp. 125–169; McGeoch et al. (1988) $J. Gen. Virol.$ 69:1531–1574; U.S. Pat. No. 5,171,568; Baer et al. (1984) $Nature$ 310:207–211; and Davison et al. (1986) $J. Gen. Virol.$ 67:1759–1816.)

Human immunodeficiency virus (HIV) antigens, such as gp120 molecules for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992); and Modrow et al. (1987) $J. Virol.$ 61:570–578) and antigen-containing genomic fragments derived or obtained from any of these isolates will find use in the present invention. Furthermore, other immunogenic proteins derived or obtained from any of the various HIV isolates will find use herein, including fragments containing one or more of the various envelope proteins such as gp160 and gp41, gag antigens such as p24gag and p55gag, as well as proteins derived from the pol, env, tat, vif, rev, nef, vpr, vpu and LTR regions of HIV.

Antigens derived or obtained from other viruses will also find use herein, such as without limitation, antigens from members of the families Picornaviridae (e.g., polioviruses, rhinoviruses, etc.); Caliciviridae; Togaviridae (e.g., rubella virus, dengue virus, etc.); Flaviviridae; Coronaviridae; Reoviridae (e.g., rotavirus, etc.); Bimaviridae; Rhabodoviridae (e.g., rabies virus, etc.); Orthomyxoviridae (e.g., influenza virus types A, B and C, etc.); Filoviridae; Paramyxoviridae (e.g., mumps virus, measles virus, respiratory syncytial virus, parainfluenza virus, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIB}$, $HIV_{SF2}$, $HIV_{LAV}$, $HIV_{LAI}$, $HIV_{MN}$); $HIV-1_{CM235}$, $HIV-1_{US4}$; HIV-2, among others; simian immunodeficiency virus (SIV); Papillomavirus, the tick-bourne encephalitis viruses; and the like. See, e.g. Virology, 3rd Edition (W. K. Joklik ed. 1988); $Fundamental Virology,$ 2nd Edition (B. N. Fields and D. M. Knipe, eds. 1991), for a description of these and other viruses.

In some contexts, it may be preferable that the selected viral antigens are obtained or derived from a viral pathogen that typically enters the body via a mucosal surface and is known to cause or is associated with human disease, such as, but not limited to, HIV (AIDS), influenza viruses (Flu), herpes simplex viruses (genital infection, cold sores, STDs), rotaviruses (diarrhea), parainfluenza viruses (respiratory infections), poliovirus (poliomyelitis), respiratory syncytial virus (respiratory infections), measles and mumps viruses (measles, mumps), rubella virus (rubella), and rhinoviruses (common cold).

Genomic fragments containing bacterial and parasitic antigens can be obtained or derived from known causative agents responsible for diseases including, but not limited to, Diptheria, Pertussis, Tetanus, Tuberculosis, Bacterial or Fungal Pneumonia, Otitis Media, Gonnorhea, Cholera, Typhoid, Meningitis, Mononucleosis, Plague, Shigellosis or Salmonellosis, Legionaire's Disease, Lyme Disease, Leprosy, Malaria, Hookworm, Onchocerciasis, Schistosomiasis, Trypamasomialsis, Lesmaniasis, *Giardia*, Amoebiasis, Filariasis, *Borelia*, and Trichinosis. Still further antigens can be obtained or derived from unconventional viruses such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

Specific pathogens can include *M. tuberculosis, Chlamydia, N. gonorrhoeae, Shigella, Salmonella, Vibrio Cholera, Treponema pallidua, Pseudomonas, Bordetella pertussis, Brucella, Franciscella tulorensis, Helicobacter pylori, Leptospria interrogaus, Legionella pneumophila, Yersinia pestis, Streptococcus* (types A and B), *Pneumococcus, Meningococcus, Hemophilus influenza* (type b), *Toxoplasma gondic, Complylobacteriosis, Moraxella catarrhalis, Donovanosis*, and *Actinomycosis*; fungal pathogens including Candidiasis and Aspergillosis; parasitic pathogens including *Taenia*, Flukes, Roundworms, Amebiasis, Giardiasis, *Cryptosporidium, Schistosoma, Pneumocystis carinii*, Trichomoniasis and Trichinosis. Thus, the present invention can also be used to provide a suitable immune response against numerous veterinary diseases, such as Foot and Mouth diseases, Coronavirus, *Pasteurella multocida, Helicobacter, Strongylus vulgaris, Actinobacillus pleuropneumonia*, Bovine viral diarrhea virus (BVDV), *Klebsiella pneumoniae, E. coli, Bordetella pertussis, Bordetella parapertussis* and *brochiseptica.*

Adjuvants

In some embodiments, the present invention may effectively be used with any suitable adjuvant or combination of adjuvants. For example, suitable adjuvants include, without limitation, adjuvants formed from aluminum salts (alum), such as aluminum hydroxide, aluminum phosphate, aluminum sulfate, etc; oil-in-water and water-in-oil emulsion formulations, such as Complete Freunds Adjuvants (CFA) and Incomplete Freunds Adjuvant (IFA); adjuvants formed from bacterial cell wall components such as adjuvants including lipopolysaccharides (e.g., lipid A or monophosphoryl lipid A (MPL), Imoto et al. (1985) *Tet. Lett.* 26:1545–1548), trehalose dimycolate (TDM), and cell wall skeleton (CWS); heat shock protein or derivatives thereof; adjuvants derived from ADP-ribosylating bacterial toxins, including diphtheria toxin (DT), pertussis toxin (PT), cholera toxin (CT), the *E. coli* heat-labile toxins (LT1 and LT2), *Pseudomonas* endotoxin A, *Pseudomonas* exotoxin S, *B. cereus* exoenzyme, *B. sphaericus* toxin, *C. botulinum* C2 and C3 toxins, C. limosum exoenzyme, as well as toxins from *C. perfringens*, C. spiriforma and *C. difficile, Staphylococcus aureus* EDIN, and ADP-ribosylating bacterial toxin mutants such as $CRM_{197}$, a non-toxic diphtheria toxin mutant (see, e.g., Bixler et al. (1989) *Adv. Exp. Med. Biol.* 251:175; and Constantino et al. (1992) Vaccine); saponin adjuvants such as Quil A (U.S. Pat. No. 5,057,540), or particles generated from saponins such as ISCOMs (immunostimulating complexes); chemokines and cytokines, such as interleukins (e.g., IL-1, IL-2, IL-4, IL-5, IL-6, IL-7, IL-8, IL-12, etc.), interferons (e.g., gama interferon), macrophage colony stimulating factor (M-CSF), tumor necrosis factor (TNF), defensins 1 or 2, RANTES, MIP1-$\alpha$ and MIP-2, etc; muramyl peptides such as N-acetyl-muramyl-L-threonyl-D-isoglutamine (thr-MDP), N-acetyl-normuramyl-$^L$-alanyl-$^D$-isoglutamine (nor-MDP), N-acetylmuramyl-$^L$-alanyl-$^D$-isoglutaminyl-$^L$-alanine-2-(1'-2'-dipalmitoyl-sn-glycero-3 huydroxyphosphoryloxy)-ethylamine (MTP-PE) etc.; adjuvants derived from the CpG family of molecules, CpG dinucleotides and synthetic oligonucleotides which comprise CpG motifs (see, e.g., Krieg et al. *Nature* (1995) 374:546, Medzhitov et al. (1997) *Curr. Opin. Immunol.* 9:4–9, and Davis et al. *J. Immunol*. (1998) 160:870–876) such as TCC ATG ACG TTC CTG ATG CT (SEQ ID NO:1) and ATC GAC TCT CGA GCG TTC TC (SEQ ID NO: 2); and synthetic adjuvants such as PCPP (Poly[di(carboxylatophenoxy)phosphazene) (Payne et al. *Vaccines* (1998) 16:92–98). Such adjuvants are commercially available from a number of distributors such as Accurate Chemicals; Ribi Immunechemicals, Hamilton, Mont.; GIBCO; Sigma, St. Louis, Mo.

The adjuvant may delivered individually or delivered in a combination of two or more adjuvants. In this regard, combined adjuvants may have an additive or a synergistic effect in promoting an immune response. A synergistic effect is one where the result achieved by combining two or more adjuvants is greater than one would expect than by merely adding the result achieved with each adjuvant when administered individually.

Preparation of Genomic Libraries

Genomic libraries can be produced by any method known in the art. A variety of sources can be used for the genomic DNA. Genomic DNA may be commercially available, for example, from sources such as Advanced Biotechnologies Inc (ABI) and Clonetech, Inc. Another standard source is, of course, genomic DNA isolated from an organism (e.g., virus, bacteria, parasite, or other pathogen), a cell (e.g., a cancer cell), or selected tissue. Alternatively, DNA can be prepared from RNA (e.g., RNA viruses) by techniques available in the art. Genomic DNA from the selected source can be isolated by standard procedures, which typically include successive phenol and phenol/chloroform extractions followed by ethanol precipitation. After precipitation, the DNA from an organism, cell or tissue of interest can be treated with a restriction endonuclease which either completely or partially digests the DNA to produce the appropriate fragments. DNA fragments of a selected size can be separated by a number of techniques, including agarose or polyacrylamide gel electrophoresis or pulse field gel electrophoresis (Carle et al. (1984) *Nuc. Acid Res.* 12:5647–5664; Chu et al. (1986) *Science* 234:1582; Smith et al. (1987) *Methods in Enzymology* 151:461), to provide an appropriate size starting material for cloning.

Another method for obtaining nucleic acid sequences for use herein is by recombinant means. Thus, a desired nucleotide sequence can be excised from a vector carrying the same using standard molecular biology procedures. Site specific DNA cleavage can be performed by treating with the suitable restriction enzyme (or enzymes) under conditions which are generally understood in the art, and the particulars of which are specified by manufacturers of commercially available restriction enzymes. If desired, size separation of the cleaved fragments may be performed by polyacrylamide gel or agarose gel electrophoresis using standard techniques.

Restriction cleaved fragments may be blunt ended, if desired, by treating with the large fragment of E. coli DNA polymerase I (Klenow) in the presence of the four deoxynucleotide triphosphates (dNTPs) using standard techniques. The Klenow fragment fills in at 5' single-stranded overhangs but digests protruding 3' single strands, even though the four dNTPs are present. If desired, selective repair can be performed by supplying only one, or several, selected dNTPs within the limitations dictated by the nature of the overhang. After Klenow treatment, the mixture can be extracted with e.g. phenol/chloroform, and ethanol precipitated. Treatment under appropriate conditions with S1 nuclease or BAL-31 results in hydrolysis of any single-stranded portion.

Once genomic fragments have been prepared or isolated, such sequences can be cloned into any suitable vector construct or replicon. Numerous cloning vectors are known to those of skill in the art, and the selection of an appropriate cloning vector is a matter of choice. In one preferred embodiment, the genomic fragments are cloned into cosmids to generate cosmid libraries. When using cosmid cloning vectors, the fragments are large, preferably between about 20,000 bp (20 kb) and 50,000 base pairs (50 kb) in size (or any integer there between), preferably between about 25 kb and 50 kb, more preferably between about 30–35 kb and 50 kb, and even more preferably between about 35 kb and about 50 kb. Suitable cosmid vectors are commercially available, for example the SuperCos 1 Cosmid Vector Kit (Stratagene, La Jolla, Calif.). Ligation of the DNA into the cosmid is performed as instructed by the manufacturer or may be empirically determined using methods known in the art in view of the teachings of this specification.

In another preferred embodiment, the genomic fragments are cloned into plasmids to generate plasmid libraries. When using plasmid cloning vectors, the fragments are typically between about 5,000 bp (5 kb) and 25,000 base pairs (25 kb) in size (or any integer there between), preferably between about 10 kb and 25 kb, more preferably between about 10–15 kb and 25 kb, and even more preferably between about 15 kb and 20 kb. Suitable plasmid vectors are commercially available. Ligation of the DNA into the plasmid is performed using methods well known in the art in view of the teachings of this specification.

As described above, one advantage of the present invention is that the large genomic fragments include endogenous transcription and translation regulatory elements. Such regulatory control sequences include, for example, promoters (a sequence associated with initiating transcription), enhancers (a cis-acting sequence that enhances transcription) and other elements including those which cause the expression of a coding sequence to be turned on or off in response to a chemical or physical stimulus, including the presence of a regulatory compound. Thus, in a preferred embodiment, the number of molecular modifications to the vectors and/or inserted polynucleotides is minimal.

It is also possible that selected nucleotide sequences within the vector constructs can be placed under the control of heterologous regulatory sequences such as a heterologous promoter, for example when the genomic fragments are derived from bacteria or other prokaryotes, and expression is desired in a eukaryotic subject. Modification of the sequences encoding the particular protein of interest may be desirable to achieve this end. For example, in some cases it may be necessary to modify the sequence so that it is attached to the control sequences with the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

Administration of Polynucleotides

The genomic fragments and ancillary substances described herein may be administered by any suitable method. In a preferred embodiment, described below, the polynucleotide fragments are administered by coating a suitable construct (e.g., cosmids or plasmids) containing the fragments onto core carrier particles and then administering the coated particles to the subject or cells. However, the genomic fragments may also be delivered using a viral vector or using non-viral systems, e.g., naked nucleic acid delivery.

Viral Vectors

A number of viral based systems have been used for gene delivery. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The genomic fragment(s) of interest can be inserted into the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors, such as the modified N2 vector described herein. Retroviral vectors can be constructed using techniques well known in the art. See, e.g., U.S. Pat. No. 5,219,740; Mann et al. (1983) Cell 33:153–159.

Adenovirus based systems have been developed for gene delivery and are suitable for delivering the genomic fragments described herein. Human adenoviruses are double-stranded DNA viruses which enter cells by receptor-mediated endocytosis. These viruses are particularly well suited for genetic transfer because they are easy to grow and manipulate and they exhibit a broad host range in vivo and in vitro. For example, adenoviruses can infect human cells of hematopoietic, lymphoid and myeloid origin. Furthermore, adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) *J. Virol.* 57:267–274; Bett et al. (1993) *J. Virol.* 67:5911–5921; Mitterederet al. (1994) *Human Gene Therapy* 5:717–729; Seth et al. (1994) *J. Virol.* 68:933–940; Barr et al. (1994) *Gene Therapy* 1:51–58; Berkner, K. L. (1988) *BioTechniques* 6:616–629; Rich et al. (1993) *Human Gene Therapy* 4:461–476.

Adeno-associated viral vectors (AAV) can also be used to administer certain of the smaller genomic fragments (e.g., 5 kb) described herein. AAV vectors can be derived from any AAV serotype, including without limitation, AAV-1, AAV-2, AAV-3, AAV-4, AAV-5, AAVX7, etc. AAV vectors can have one or more of the AAV wild-type genes deleted in whole or in part, preferably the rep and/or cap genes, but retain one or more functional flanking inverted terminal repeat (ITR) sequences. A functional ITR sequence is generally deemed necessary for the rescue, replication and packaging of the AAV virion. Thus, an AAV vector includes at least those sequences required in cis for replication and packaging (e.g., a functional ITR) of the virus. The ITR need not be the wild-type nucleotide sequence, and may be altered, e.g., by the insertion, deletion or substitution of nucleotides, so long as the sequence provides for functional rescue, replication and packaging.

AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is bounded (5' and 3') with functional AAV ITR sequences. Suitable AAV constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Conventional Pharmaceutical Preparations

Formulation of a preparation comprising the genomic DNA fragments of the present invention, with or without addition of an adjuvant composition, can be carried out using standard pharmaceutical formulation chemistries and methodologies all of which are readily available to the ordinarily skilled artisan. For example, compositions containing one or more genomic fragments (e.g., present in a plasmid or cosmid) can be combined with one or more pharmaceutically acceptable excipients or vehicles to provide a liquid preparation.

Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that the preparation will contain a pharmaceutically acceptable excipient that serves as a stabilizer, particularly for peptide, protein or other like molecules if they are to be included in the vaccine composition. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

Certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, e.g., *Liposomes: A Practical Approach*, (1990) RPC New Ed., IRL Press). Cationic lipid preparations are also well known vehicles for use in delivery of nucleic acid molecules. Suitable lipid preparations include DOTMA (N-[1-(2,3-dioleyloxy)propyl]-N,N,N-trimethylammonium chloride), available under the tradename Lipofectin™, and DOTAP (1,2-bis(oleyloxy)-3-(trimethylammonio)propane), see, e.g., Felgner et al. (1987) *Proc. Natl. Acad. Sci. USA* 84:7413–7416; Malone et al. (1989) *Proc. Natl. Acad. Sci. USA* 86:6077–6081; U.S. Pat. Nos. 5,283,185 and 5,527,928, and International Publication Nos WO 90/11092, WO 91/15501 and WO 95/26356. These cationic lipids may preferably be used in association with a neutral lipid, for example DOPE (dioleyl phosphatidylethanolamine). Still further transfection-facilitating compositions that can be added to the above lipid or liposome preparations include spermine derivatives (see, e.g., International Publication No. WO 93/18759) and membrane-permeabilizing compounds such as GALA, Gramicidine S and cationic bile salts (see, e.g., International Publication No. WO 93/19768).

Alternatively, the nucleic acid molecules of the present invention may be encapsulated, adsorbed to, or associated with, particulate carriers. Suitable particulate carriers include those derived from polymethyl methacrylate polymers, as well as PLG microparticles derived from poly (lactides) and poly(lactide-co-glycolides). See, e.g., Jeffery et al. (1993) *Pharm. Res.* 10:362–368. Other particulate systems and polymers can also be used, for example, polymers such as polylysine, polyarginine, polyornithine, spermine, spermidine, as well as conjugates of these molecules.

The formulated vaccine compositions will thus typically include a polynucleotide (e.g., a plasmid or cosmid) containing at least one genomic fragment from a selected pathogen in an amount sufficient to mount an immunological response. An appropriate effective amount can be readily determined by one of skill in the art. Such an amount will fall in a relatively broad range that can be determined through routine trials. For example, immune responses have been obtained using as little as 1 µg of DNA, while in other administrations, up to 2 mg of DNA has been used. It is generally expected that an effective dose of polynucleotides containing the genomic fragments will fall within a range of about 10 μg to 1000 μg, however, doses above and below this range may also be found effective. The compositions may thus contain from about 0.1% to about 99.9% of the polynucleotide molecules.

Administration of Conventional Pharmaceutical Preparations

Administration of the above-described pharmaceutical preparations can be effected in one dose, continuously or intermittently throughout the course of treatment. Delivery will most typically be via conventional needle and syringe for the liquid compositions and for liquid suspensions containing particulate compositions. In addition, various liquid jet injectors are known in the art and may be employed to administer the present compositions. Methods of determining the most effective means and dosages of administration are well known to those of skill in the art and will vary with the delivery vehicle, the composition of the therapy, the target cells, and the subject being treated. Single and multiple administrations can be carried out with the dose level and pattern being selected by the attending physician. It should be understood that more than one genomic fragment can be carried by the delivered polynucleotide vector construct. Alternatively, separate vectors (e.g., cosmids or plasmids), each expressing one or more antigens derived from any pathogen can also be delivered to a subject as described herein.

Furthermore, it is also intended that the polynucleotides delivered by the methods of the present invention be combined with other suitable compositions and therapies. For instance, in order to augment an immune response in a subject, the compositions and methods described herein can further include ancillary substances (e.g., adjuvants), such as pharmacological agents, cytokines, or the like. Ancillary substances may be administered, for example, as proteins or other macromolecules at the same time, prior to, or subsequent to, administration of the DNA vaccines (e.g., cosmids or plasmids) described herein. The nucleic acid molecule compositions may also be administered directly to the subject or, alternatively, delivered ex vivo, to cells derived from the subject, using methods known to those skilled in the art.

Coated Particles

In one embodiment, constructs containing the genomic fragments (e.g, plasmids or cosmids), and other ancillary components such as adjuvants are delivered using carrier particles. Particle-mediated delivery methods for administering such nucleic acid preparations are known in the art. Thus, once prepared and suitably purified, the above-described plasmid and cosmid constructs can be coated onto carrier particles (e.g., core carriers) using a variety of techniques known in the art. Carrier particles are selected from materials which have a suitable density in the range of particle sizes typically used for intracellular delivery from an appropriate particle delivery device. The optimum carrier particle size will, of course, depend upon the diameter of the target cells.

For the purposes of the present invention, tungsten, gold, platinum and iridium core carrier particles can be used. Tungsten and gold particles are preferred. Tungsten particles are readily available in average sizes of 0.5 to 2.0 μm in diameter. Although such particles have optimal density for use in particle delivery methods, and allow highly efficient coating with DNA, tungsten may potentially be toxic to certain cell types. Accordingly, gold particles or microcrystalline gold (e.g., gold powder A1570, available from Engelhard Corp., East Newark, N.J.) will also find use with the present methods. Gold particles provide uniformity in size (available from Alpha Chemicals in particle sizes of 1–3 μm, or available from Degussa, South Plainfield, N.J. in a range of particle sizes including 0.95 μm) and reduced toxicity.

A number of methods are known and have been described for coating or precipitating DNA or RNA onto gold or tungsten particles. Most such methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module or cassette, or loaded into a delivery cassette for use in a suitable particle delivery device.

Peptide adjuvants (e.g., cytokines and bacterial toxins), can also be coated onto the same or similar core carrier particles. For example, peptides can be attached to a carrier particle by simply mixing the two components in an empirically determined ratio, by ammonium sulfate precipitation or other solvent precipitation methods familiar to those skilled in the art, or by chemical coupling of the peptide to the carrier particle. The coupling of L-cysteine residues to gold has been previously described (Brown et al., *Chemical Society Reviews* 9:271–311 (1980)). Other methods would include, for example, dissolving the peptide adjuvant in absolute ethanol, water, or an alcohol/water mixture, adding the solution to a quantity of carrier particles, and then drying the mixture under a stream of air or nitrogen gas while vortexing. Alternatively, the adjuvant can be dried onto carrier particles by centrifugation under vacuum. Once dried, the coated particles can be resuspended in a suitable solvent (e.g., ethyl acetate or acetone), and triturated (e.g., by sonication) to provide a substantially uniform suspension. The core carrier particles coated with the adjuvant can then be combined with core carrier particles carrying the genomic fragment constructs and administered in a single particle injection step, or administered separately from the genomic fragment compositions.

Administration of Coated Particles

Following their formation, core carrier particles coated with the nucleic acid preparations of the present invention, alone or in combination with e.g., adjuvant preparations, are delivered to a subject using particle-mediated delivery techniques.

Various particle delivery devices suitable for particle-mediated delivery techniques are known in the art, and are all suited for use in the practice of the invention. Current device designs employ an explosive, electric or gaseous discharge to propel the coated core carrier particles toward target cells. The coated particles can themselves be releasably attached to a movable carrier sheet, or removably attached to a surface along which a gas stream passes, lifting the particles from the surface and accelerating them toward the target. An example of a gaseous discharge device is described in U.S. Pat. No. 5,204,253. An explosive-type device is described in U.S. Pat. No. 4,945,050. One example of an electric discharge-type particle acceleration apparatus is described in U.S. Pat. No. 5,120,657. Another electric discharge apparatus suitable for use herein is described in U.S. Pat. No. 5,149,655. The disclosure of all of these patents is incorporated herein by reference in their entireties.

The coated particles are administered to the subject to be treated in a manner compatible with the dosage formulation, and in an amount that will be effective to bring about a desired immune response. The amount of the composition to be delivered which, in the case of nucleic acid molecules is generally in the range of from 0.001 to 100.0 µg, more typically 0.01 to 10.0 µg of nucleic acid molecule per dose, and in the case of peptide or protein molecules is 1 µg to 5 mg, more typically 1 to 50 µg of peptide, depends on the subject to be treated. The exact amount necessary will vary depending on the age and general condition of the individual being immunized and the particular nucleotide sequence or peptide selected, as well as other factors. An appropriate effective amount can be readily determined by one of skill in the art upon reading the instant specification.

Thus, an effective amount of the genomic fragments herein described will be sufficient to bring about a suitable immune response in an immunized subject, and will fall in a relatively broad range that can be determined through routine trials. Preferably, the coated core particles are delivered to suitable recipient cells in order to bring about an immune response (e.g., T-cell activation) in the treated subject.

Particulate Compositions

Alternatively, the genomic fragments of the present invention (e.g. plasmid or cosmid constructs carrying the genomic fragments), as well as one or more selected adjuvants, can be formulated as a particulate composition. More particularly, formulation of particles comprising a genomic fragment of interest can be carried out using standard pharmaceutical formulation chemistries and methodologies all of which are readily available to the reasonably skilled artisan. For example, one or more vector construct and/or adjuvants can be combined with one or more pharmaceutically acceptable excipients or vehicles to provide a vaccine composition. Auxiliary substances, such as wetting or emulsifying agents, pH buffering substances, and the like, may be present in the excipient or vehicle. These excipients, vehicles and auxiliary substances are generally pharmaceutical agents that do not themselves induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that the nucleic acid composition will contain a pharmaceutically acceptable carrier that serves as a stabilizer, particularly for peptide, protein or other like adjuvants or ancillary materials. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. A thorough discussion of pharmaceutically acceptable excipients, carriers, stabilizers and other auxiliary substances is available in REMINGTONS PHARMACEUTICAL SCIENCES (Mack Pub. Co., N.J. 1991), incorporated herein by reference.

The formulated compositions will include an amount of the genomic fragment of interest which is sufficient to mount an immunological response, as defined above. An appropriate effective amount can be readily determined by one of skill in the art. Such an amount will fall in a relatively broad range, generally within the range of about 0.1 µg to 25 mg or more of the nucleic acid construct of interest, and specific suitable amounts can be determined through routine trials. The compositions may contain from about 0.1% to about 99.9% of the nucleic acid molecule. If an adjuvant is included in the composition, or the methods are used to provide a particulate adjuvant composition, the adjuvant will be present in a suitable amount as described above. The compositions are then prepared as particles using standard techniques, such as by simple evaporation (air drying), vacuum drying, spray drying, freeze drying (lyophilization), spray-freeze drying, spray coating, precipitation, supercritical fluid particle formation, and the like. If desired, the resultant particles can be densified using the techniques described in commonly owned International Publication No. WO 97/48485, incorporated herein by reference.

Single unit dosages or multidose containers, in which the particles may be packaged prior to use, can comprise a hermetically sealed container enclosing a suitable amount of the particles comprising a suitable nucleic acid construct (e.g., a plasmid or cosmid) and/or the selected adjuvant (e.g., to provide a vaccine composition). The particulate compositions can be packaged as a sterile formulation, and the hermetically sealed container can thus be designed to preserve sterility of the formulation until use in the methods of the invention. If desired, the containers can be adapted for direct use in a particle delivery device. Such containers can take the form of capsules, foil pouches, sachets, cassettes, and the like. Appropriate particle delivery devices (e.g., needleless syringes) are described herein.

The container in which the particles are packaged can further be labelled to identify the composition and provide relevant dosage information. In addition, the container can be labelled with a notice in the form prescribed by a governmental agency, for example the Food and Drug Administration, wherein the notice indicates approval by the agency under Federal law of the manufacture, use or sale of the antigen, adjuvant (or vaccine composition) contained therein for human administration.

The particulate compositions (comprising one or more genomic fragments of interest alone, or in combination with a selected adjuvant) can then be administered using a transdermal delivery technique. Preferably, the particulate compositions will be delivered via a powder injection method, e.g., delivered from a needleless syringe system such as those described in commonly owned International Publication Nos. WO 94/24263, WO 96/04947, WO 96/12513, and WO 96/20022, all of which are incorporated herein by reference. Delivery of particles from such needleless syringe systems is typically practised with particles having an approximate size generally ranging from 0.1 to 250 µm, preferably ranging from about 10–70 µm. Particles larger than about 250 µm can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin tissue. In this regard, optimal particle densities for use in needleless injection generally range between about 0.1 and 25 g/cm$^3$, preferably between about 0.9 and 1.5 g/cm$^3$, and injection velocities generally range between about 100 and 3,000 m/sec, or greater. With appropriate gas pressure, particles having an average diameter of 10–70 µm can be accelerated through the nozzle at velocities approaching the supersonic speeds of a driving gas flow.

If desired, these needleless syringe systems can be provided in a preloaded condition containing a suitable dosage of the particles comprising the genomic fragments and/or the selected adjuvant. The loaded syringe can be packaged in a hermetically sealed container, which may further be labelled as described above.

Thus, the method can be used to obtain nucleic acid particles having a size ranging from about 10 to about 250 µm, preferably about 10 to about 150 µm, and most preferably about 20 to about 60 µm; and a particle density ranging from about 0.1 to about 25 g/cm$^3$, and a bulk density of about 0.5 to about 3.0 g/cm$^3$, or greater.

Similarly, particles of selected adjuvants having a size ranging from about 0.1 to about 250 µm, preferably about 0.1 to about 150 µm, and most preferably about 20 to about 60 µm; a particle density ranging from about 0.1 to about 25 g/cm$^3$, and a bulk density of preferably about 0.5 to about 3.0 g/cm$^3$, and most preferably about 0.8 to about 1.5 g/cm$^3$ can be obtained.

Administration of Particulate Compositions

Following their formation, the particulate compositions (e.g., powder) can be delivered transdermally to the tissue of a vertebrate subject using a suitable transdermal delivery technique. Various particle delivery devices suitable for administering the substance of interest are known in the art, and will find use in the practice of the invention. A particularly preferred transdermal particle delivery system employs a needleless syringe to fire solid particles in controlled doses into and through intact skin and tissue. See, e.g., U.S. Pat. No. 5,630,796 to Bellhouse et al. which describes a needleless syringe (also known as "the PowderJect® particle delivery device"). Other needleless syringe configurations are known in the art and are described herein.

Compositions containing a therapeutically effective amount of the powdered molecules described herein can be delivered to any suitable target tissue via the above-described particle delivery devices. For example, the compositions can be delivered to muscle, skin, brain, lung, liver, spleen, bone marrow, thymus, heart, lymph, blood, bone cartilage, pancreas, kidney, gall bladder, stomach, intestine, testis, ovary, uterus, rectum, nervous system, eye, gland and connective tissues. For nucleic acid molecules, delivery is preferably to, and the molecules expressed in, terminally differentiated cells; however, the molecules can also be delivered to non-differentiated, or partially differentiated cells such as stem cells of blood and skin fibroblasts.

The powdered compositions are administered to the subject to be treated in a manner compatible with the dosage formulation, and in an amount that will be prophylactically and/or therapeutically effective. The amount of the composition to be delivered, generally in the range of from 0.5 µg/kg to 100 µg/kg of nucleic acid molecule per dose, depends on the subject to be treated. Doses for other pharmaceuticals, such as physiological active peptides and proteins, generally range from about 0.1 µg to about 20 mg, preferably 10 µg to about 3 mg. The exact amount necessary will vary depending on the age and general condition of the individual to be treated, the severity of the condition being treated, the particular preparation delivered, the site of administration, as well as other factors. An appropriate effective amount can be readily determined by one of skill in the art.

Thus, a "therapeutically effective amount" of the present particulate compositions will be sufficient to bring about treatment or prevention of disease or condition symptoms, and will fall in a relatively broad range that can be determined through routine trials.

Below are examples of specific embodiments for carrying out the present invention. The examples are offered for illustrative purposes only, and are not intended to limit the scope of the present invention in any way.

EXAMPLES

Efforts have been made to ensure accuracy with respect to numbers used (e.g., amounts, temperatures, etc.), but some experimental error and deviation should, of course, be allowed for.

Example 1

Nucleic Acid Immunization Using HSV-2 Cosmids

In order to assess the specificity and effectiveness of nucleic acid immunization using DNA vaccine cosmids containing HSV-2 genomic DNA, the following studies were carried out.

A. Cosmid Preparation

HSV-2 Cosmids:

HSV-2 genomic DNA was obtained by infecting Vero cells (ATCC # CCL-81) with HSV-2 strain MS (ATCC # VR-54T) and isolating genomic DNA from the infected cells. Cosmids containing fragments of the HSV-2 genome were generated by digesting HSV-2 genomic DNA, as described above, with the restriction enzyme EcoRI (New England Biolabs). As shown in FIG. 1, the HSV genome has been mapped and contains at least 10 EcoRI sites, indicated in the figure with arrows. The digested DNA was ligated into cosmids using the SuperCos 1 Cosmid Vector Kit from Stratagene following the manufacturers instructions. Positive cosmids were first identified from the fragment sizes generated by an EcoRI digest of purified cosmid DNA. The digested DNA was loaded onto a 1% agarose gel (15 hour pulse field electrolysis, run time at 6 V/cm, 120° angle, 14° C. in 0.5×TBE buffer). Further identification was based on restriction maps generated with other restriction enzymes. This preliminary analysis was used to determine fragment locations relative to the HSV-2 genome shown in FIG. 1. For example, cosmid #68 contains a fragment of the HSV-2 genome extending from the 7th to 10th EcoRI sites shown, while clone #74 contains an HSV-2 fragment extending from the 1 st through 4th depicted EcoR1 sites.

B. Preparation of Coated Microparticles

Cosmid DNA was coated onto 1–3 µm gold particles (Degussa Corp., South Plainfield, N.J.) using techniques described by Eisenbraun et al. (1993) *DNA Cell Biol.* 12:791–797. Briefly, cosmid DNA was affixed to gold particles by adding 13.26 mg of 1–3 micron gold powder (Degussa) and an appropriate amount of cosmid DNA (2 µg per mg of gold powder) to a 1.5 ml centrifuge tube containing 500 µl of 0.05 M spermidine (Sigma). Cosmid DNA and gold were coprecipitated by the addition of 500 µl of 10% $CaCl_2$ (Fujisawa) dropwise while vortexing, after which the precipitate was allowed to settle for several minutes. The gold/DNA precipitate was concentrated by centrifugation in a microcentrifuge for 15 seconds, washed three time in absolute ethanol (Spectrum) and resuspended in an appropriate amount of ethanol (8.84 mg gold powder/ml of ethanol) and polyvinyl pyrrilodine (PVP) (Spectrum) 0.05 mg/ml of ethanol. The suspension was then transferred to a glass vial which was capped and immersed in a sonicating water bath for 2–5 seconds to resolve clumps. The ethanol solution was then injected into Tefzel tubing (McMaster-Carr) and the gold/DNA adhered to the side of the tubing using centrifugal force. The remaining ethanol was then ejected using a small, controlled flow of nitrogen gas. The tube was then dried for one hour with a flow of nitrogen gas, and then cut into half inch cartridges. The cartridges were stored in a tightly capped glass scintillation vials with dessicant at 4° C. until use.

The DNA-coated gold particles were then loaded into Tefzel® tubing as described in U.S. Pat. No. 5,584,807 to McCabe, and the tubing was cut into 1.27 cm lengths to serve as cartridges in a particle delivery device. The helium-pulse PowderJect® XR particle delivery device has been previously described (see, U.S. Pat. No. 5,584,807) and was obtained from PowderJect Vaccines, Madison, Wis. In the vaccinations, each 1.27 cm cartridge nominally contained 0.5 mg gold particles coated with 1 µg of DNA.

C. Immunizations

Balb/c mice were immunized by particle-mediated delivery using a single shot of gold beads coated with cosmid (approximately 1 µg cosmid/mg gold, 0.5 mg gold delivered per shot). Animals were boosted 4 weeks after priming. Serum was collected at the time of boosting (4 week) and two weeks later (6 week).

Figure 2:
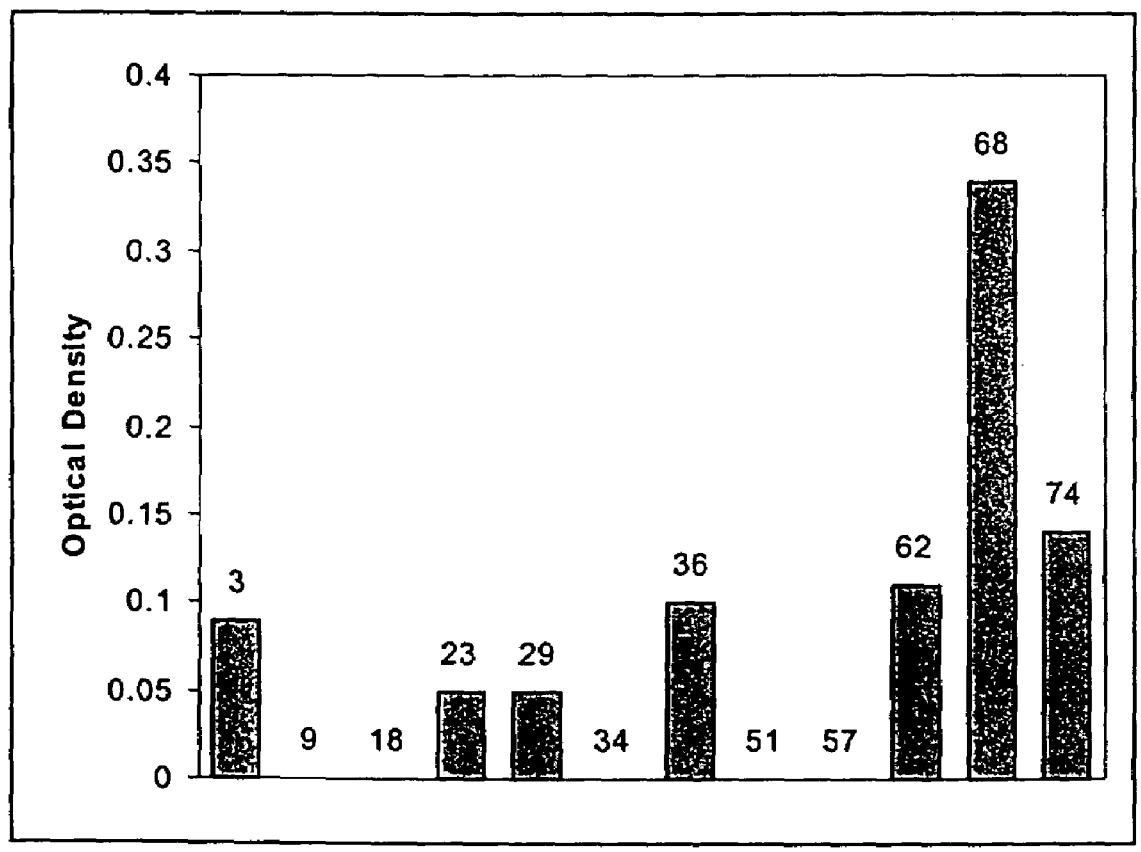
FIG. 2 depicts serum antibody levels in mice immunized with HSV-2 cosmids.

Serum antibody levels in mice at 6 weeks were detected using an ELISA. Briefly, HSV-2 antigen was prepared at a concentration of 10 µg/ml in PBS. One hundred microliters of the HSV-2 antigen preparation was added to each well of a 96 well plates (Costar), for a concentration of approximate 1 µg of protein/well. The plates were incubated overnight at 4° C. and then washed 3 times with PBS/0.05% Tween 20 solution. The plates were blocked with PBS/Tween with 5% dry milk for 1 hour at room temperature. Dilute rabbit anti-HSV-2 (control) antibody or mouse serum (unknowns) at 1:100 in PBS/Tween was added to appropriate wells. The plates were washed 3 times with PBS/0.05% Tween 20. A 1:8000 dilution of biotin conjugated goat anti-rabbit in PBS/Tween was prepared and 100 µl added to each well. The plates were washed 3 times with PBS/0.05% Tween 20. A 1:8000 dilution of streptavidin-HRP was prepared, 100 µl added to each well for a 1 hour incubation at room temperature. The plates were washed 6 times with PBS/0.05% Tween 20. TMB was prepared just prior to use, 100 µl added to each well and incubated for 15 at room temperature. Reactions were stopped by the addition of 100 µl 1 N $H_2SO_4$ and optical density values read on an automated plate reader at 450 nm. Values from the 1:160 dilution were averaged for the individual animals (4 per group) and the optical density of the control group (animals vaccinated with empty vector) was subtracted. Results for particular cosmids are shown in FIG. 2. The numbers above the bars are the names of the different cosmid clones.

D. Cell Mediated Immune Response

Spleen cell proliferation assays were done to further assess the ability of an HSV-2 genome-derived cosmid to induce a cell-mediated immune (CMI) response. This assay measures the capacity of spleen-derived lymphocytes cultured in vitro to proliferate, i.e., grow and divide thus increasing in number, in response to HSV-2 antigens. The greater the amount of proliferation, as assessed by a higher stimulation index score, the stronger the immune response against the antigens.

BALB/c mice were immunized with either a plasmid containing the gene for expression of the HSV-2 gD-antigen PCR amplified from HSV-2 genomic DNA cloned into a pTarget vector (Promega), or with a HSV-2 genomic-derived cosmid (designated No. 68 as described above). A PowderJect® XR particle delivery device was used to vaccinate the mice by delivery of plasmid/cosmid DNA-coated gold-particles into the epidermis. Mice were immunized with a prime and two boosts (each given 4 weeks apart). Each immunization consisted of a single injection that delivered 1 µg of DNA/0.5 mg gold. These mice had also been injected in their ear pinna with protein extracts (100 µg in PBS), 1–2 weeks after the third boost immunization, to assess their ability to mount a delayed-type hypersensitivity response. The right and left ears of these animals were injected with protein extracts derived from HSV-2 infected and uninfected cultured VERO cells (ATCC #CCL-81), respectively.

Figure 3:
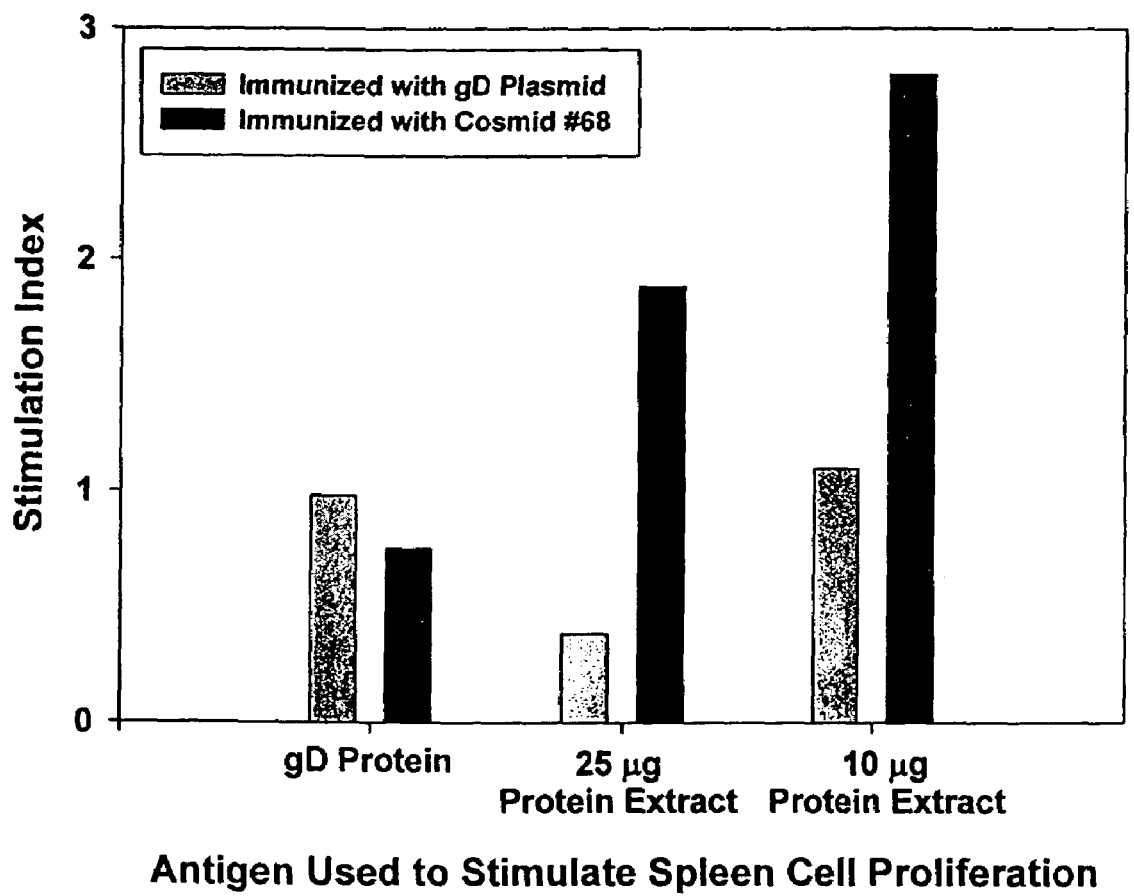
FIG. 3 depicts antigen-specific spleen cell proliferation in animals immunized with either an HSV-2 gD plasmid or an HSV-2 cosmid.

Three weeks after protein injection two mice were sacrificed from each immunization group (designated in the figure legend-box as "gD Plasmid and Cosmid #68"), along with two non-immune naïve mice. The spleen cells from these animals were isolated and cultured in vitro with either pure gD protein (0.1 µg/well), or HSV-2 infected VERO cell protein extract (25 or 10 µg/well), or no added antigen. After 3 days in culture the antigen induced proliferation responses of the different spleen cell populations were quantified by the amount of radioactively labeled thymidine that was incorporated into the dividing cells (measured as counts per minute in a scintillation counter). Stimulation indices were calculated by dividing the amount of radioactivity, i.e., counts per minute (cpm), incorporated within antigen-stimulated spleen cells by the cpm of their non-antigen-stimulated spleen cell counterparts. In FIG. 3, the stimulation indices of the antigen-stimulated non-immune naïve spleen cells were subtracted from that of the spleen cells derived from the immunized mice to give a true representation of the level of antigen-specific cell-mediated immunity elicited by the gD-antigen expressing plasmid compared to that elicited by the HSV-2 genomic-derived cosmid.

These results clearly demonstrate that the HSV-2 genomic-derived cosmid #68 is capable of eliciting a strong CMI response against HSV-2 antigens in mice. The CMI response to gD protein was slightly higher for spleen cells obtained from gD plasmid immunized mice compared to that of spleen cells obtained from mice immunized with cosmid #68. In contrast, the CMI response to protein extract from HSV-2 infected VERO cells, which contains a multiple array of HSV-2 antigens, was significantly higher for the spleens cells obtained from the mice immunized with cosmid #68 compared to that of the spleen cells obtained from the mice immunized with the single gD-antigen expressing plasmid. Thus, these data demonstrate the utility of using a cosmid-based DNA-vaccine to produce a stronger CMI response.

Similarly experiments were carried out with above-described HSV-2 genomic-derived cosmids in a guinea pig animal model system. The cosmids also elicited a strong CMI response in these animals. In subsequent challenge studies in the immunized guinea pigs, protective immunity was not observed; however, these results were deemed inconclusive.

Example 2

Nucleic Acid Immunization Using HSV-2 Plasmids

A. Plasmid Construction

HSV-2 genomic DNA was obtained by infecting VERO cells (ATCC #CCL-81) with HSV-2 strain MS (ATCC

VR-54T) and isolating genomic DNA from purified viral particles. PCR was performed using the genomic DNA to amplify segments for cloning into a plasmid vector.

The primer gB2, having the following sequence: CGC GTC TAG AAA CGT TCG CGA CCA CGG GTG AC (SEQ ID NO: 3) and primer gB3, having the following sequence: CGC GTC TAG ATG ATG GGG TCC CGC TAA CTC GC (SEQ ID NO: 4), which correspond to sequences at 58160 and 52930 of the HSV-2 genome, respectively, were used to amplify a product of approximately 5200 bp by PCR. A second PCR product was generated with using primer gB2 (SEQ ID NO: 3) and primer gB4, having the following sequence: CGC GTC TAG ACC TTC ATG ACC GCG CTG GTC CT (SEQ ID NO: 5) which correspond to sequences at 58160 and 49670, respectively, of the HSV-2 genome. This produced a product of approximately 8500 bp. Both products contain the genomic sequences coding for the glycoprotein B protein.

The PCR cycle specifications were: 98° C. 30 seconds, 70° C. 10 minutes, for 35 cycles. PCR reactions were carried out using the Expand Long template PCR system (Boehringer Mannheim). Reaction conditions were 20 pmoles of each primer, 1 μg of HSV-2 genomic DNA, 1× buffer #1 (5 mM Tris-HCl, pH 9.2, 1.6 mM $(NH_4)_2SO_4$, 1.75 mM $MgCl_2$), 200 μM deoxynucleotides (dNTPs, Sigma), 1% DMSO, 10 mM $MgSO_4$, $H_2O$ to 50 μL and 1U of Expand DNA polymerase. PCR products were "A-tailed" by incubating the products with 1U Taq DNA polymerase (Promega) for 10 minutes at 72° C. after the addition of an additional 100 μM dNTPs. The PCR fragments were purified from agarose gels and ligated into pGEM-T Easy vector system (Promega) using manufacturers instructions. TOP 10 E. coli competent bacteria (Stratagene) were transformed with the ligation mixtures by electroporation and bacteria retaining plasmid were isolated on agar plates prepared with ampicillin. DNA minipreps were made from overnight cultures of selected bacterial colonies and purified plasmids were tested for the desired inserts. Mobility on agarose gels and an appropriate restriction pattern was used to identify positive plasmids.

B. Preparation of Coated Microparticles

Plasmid DNA was coated onto 1–3 μm gold particles (Degussa Corp., South Plainfield, N.J.) using techniques described by Eisenbraun et al. (1993) *DNA Cell Biol.* 12:791–797. Briefly, plasmid DNA was affixed to gold particles by adding gold powder and an appropriate amount of plasmid DNA to a centrifuge tube containing spermidine. Plasmid DNA and gold were coprecipitated by the addition of $CaCl_2$ (Fujisawa) dropwise while vortexing, after which the precipitate was allowed to settle for several minutes. The gold/DNA precipitate was concentrated by centrifugation in a microcentrifuge, washed three time in absolute ethanol and resuspended in an appropriate amount of ethanol and polyvinyl pyrrilodine (PVP). The suspension was then transferred to a glass vial which was capped and immersed in a sonicating water bath for 2–5 seconds to resolve clumps. The ethanol solution was then injected into Tefzel® tubing (McMaster-Carr) and the gold/DNA adhered to the side of the tubing using centrifugal force. The remaining ethanol was then removed using a small, controlled flow of nitrogen gas. The tube was then dried for with a flow of nitrogen gas, and then cut into cartridges. The cartridges were stored in a tightly capped glass scintillation vials with dessicant at 4° C. until use.

C. Immunizations

C57/black mice were immunized by particle-mediated delivery using a single shot of gold beads coated with plasmid (approximately 2 μg plasmid/mg gold, 0.5 mg gold delivered per shot). Animals are boosted 4 weeks after priming. Serum is collected at the time of boosting (4 week) and is also collected two weeks later (6 week).

Serum antibody levels in mice at 6 weeks is detected using an ELISA substantially identical to that described in Example 1 above. Spleen cell proliferation assays are also carried out to further assess the ability of an HSV-2 genome-derived plasmid to induce a cell-mediated immune (CMI) response.

Thus, this study demonstrates the utility of using a plasmid-based DNA-vaccine to elicit an immune response.

Accordingly, novel compositions for eliciting an immune response have been described. Methods of using these compositions have also been described. Although preferred embodiments of the subject invention have been described in some detail, it is understood that obvious variations can be made without departing from the spirit and the scope of the invention as defined by the appended claims.

What is claimed is:

1. A method for eliciting an immune response in a vertebrate subject, said method comprising: administering core carriers coated with a vector construct to a subject using a particle-mediated transdermal delivery technique, wherein (a) the vector construct carries an HSV genomic DNA fragment or HSV genomic DNA fragments, the fragment or fragments expressing HSV antigens consisting essentially of those encoded by the HSV immediate early genes ICP 27, ICP 0, ICP 4 and ICP 22; (b) the ICP 27, ICP 0, ICP 4 and ICP 22 antigens are expressed in the subject in an amount sufficient to elicit an immune response; and (c) the vector construct is selected from the group consisting of (i) a plasmid comprising an HSV genomic DNA fragment which is, or HSV genomic DNA fragments which collectively are, between about 5 kilobases and about 25 kilobases in size and (ii) a cosmid comprising a HSV genomic DNA fragment which is, or HSV genomic DNA fragments which collectively are, between about 25 kilobases and about 50 kilobases in size.

2. The method of claim 1, wherein expression of coding sequences contained within the genomic DNA fragments is not driven by a heterologous promoter.

3. The method of claim 1, wherein the vector construct is a plasmid and the genomic fragments are collectively between about 5 kilobases and about 25 kilobases in size.

4. The method of claim 1, wherein the core carriers have an average diameter of about 0.5 to about 5 μm and a density sufficient to allow delivery into the subject.

5. The method of claim 4, wherein the core carriers are comprised of a metal.

6. The method of claim 5, wherein the metal is gold.

7. The method of claim 1, wherein step (b) is repeated to provide a prime and a booster administration.

8. The method of claim 1, wherein the vector construct is a cosmid and the genomic fragments are collectively between about 25 kilobases and about 50 kilobases in size.

9. The method of claim 8, wherein the core carriers have an average diameter of about 0.5 to about 5 μm and a density sufficient to allow delivery into the subject.

10. The method of claim 9, wherein the core carriers are comprised of a metal.

11. The method of claim 10, wherein the metal is gold.

12. The method of claim 8, wherein step (b) is repeated to provide a prime and a booster administration.

* * * * *